(12) United States Patent
Jobert

(10) Patent No.: US 11,221,289 B2
(45) Date of Patent: Jan. 11, 2022

(54) OPTICAL PARTICLE DETECTOR

(71) Applicant: COMMISSARIAT A L'ENERGIE ATOMIQUE ET AUX ENERGIES ALTERNATIVES, Paris (FR)

(72) Inventor: Gabriel Jobert, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 35 days.

(21) Appl. No.: 16/722,183

(22) Filed: Dec. 20, 2019

(65) Prior Publication Data

US 2020/0292436 A1 Sep. 17, 2020

(30) Foreign Application Priority Data

Dec. 21, 2018 (FR) ...................... 18 74073

(51) Int. Cl.
| | |
|---|---|
| *G01N 15/06* | (2006.01) |
| *G01N 33/00* | (2006.01) |
| *G01N 33/18* | (2006.01) |
| *G08B 17/107* | (2006.01) |

(52) U.S. Cl.
CPC ......... *G01N 15/06* (2013.01); *G01N 33/0057* (2013.01); *G01N 33/18* (2013.01); *G08B 17/107* (2013.01); *G01N 2015/0693* (2013.01)

(58) Field of Classification Search
CPC .................................................. G01N 15/06
USPC ........................................................ 356/222
See application file for complete search history.

(56) References Cited

U.S. PATENT DOCUMENTS

| | | | | | |
|---|---|---|---|---|---|
| 4,953,978 | A | * | 9/1990 | Bott | ................. G01N 15/0211 356/336 |
| 5,946,091 | A | * | 8/1999 | Yufa | ................. G01N 15/0205 356/336 |
| 6,519,033 | B1 | * | 2/2003 | Quist | ................. G01N 15/14 356/337 |

(Continued)

FOREIGN PATENT DOCUMENTS

| | | |
|---|---|---|
| FR | 2 963 101 A1 | 1/2012 |
| WO | WO 2004/019031 A1 | 3/2004 |
| WO | WO 2016/001324 A1 | 1/2016 |

OTHER PUBLICATIONS

French Preliminary Search Report dated Nov. 18, 2019 in French Application 18 74073 filed Dec. 21, 2018 (with English Translation of Categories of Cited Documents & Written Opinion), 14 pages.

*Primary Examiner* — Tarifur R Chowdhury
*Assistant Examiner* — Omar H Nixon
(74) *Attorney, Agent, or Firm* — Oblon, McClelland, Maier & Neustadt, L.L.P.

(57) ABSTRACT

An optical detector for particles is provided, including: a channel configured to receive a fluid including at least one particle and to receive at least one incident light ray; a detection system including a plurality of photodetectors, each photodetector being configured to receive light rays coming from the channel and diffused by the at least one particle; and an angular filtering system including a plurality of angular filtering devices each associated with a photodetector of the plurality of photodetectors, each angular filtering device being configured to angularly filter the light rays coming from the channel before reception thereof by the photodetector with which it is associated.

21 Claims, 8 Drawing Sheets

(56) References Cited

U.S. PATENT DOCUMENTS

| | | | |
|---|---|---|---|
| 7,057,724 B1* | 6/2006 | Mead | G01N 15/1459 |
| | | | 356/343 |
| 9,518,909 B2 | 12/2016 | Nicoletti | |
| 2003/0035105 A1* | 2/2003 | Quist | G01N 15/14 |
| | | | 356/338 |
| 2004/0038413 A1 | 2/2004 | Kramer | |
| 2004/0144935 A1* | 7/2004 | Xu | G01N 15/0211 |
| | | | 250/573 |
| 2004/0197232 A1 | 10/2004 | Kramer | |
| 2005/0195605 A1* | 9/2005 | Saccomanno | G02B 6/4206 |
| | | | 362/268 |
| 2005/0243307 A1* | 11/2005 | Silcott | G01N 15/1459 |
| | | | 356/73 |
| 2010/0288921 A1* | 11/2010 | Wang | G01N 15/1459 |
| | | | 250/287 |
| 2012/0257193 A1* | 10/2012 | Hummel | G01N 21/645 |
| | | | 356/73.1 |
| 2014/0247444 A1* | 9/2014 | Babico | G01N 21/49 |
| | | | 356/72 |
| 2014/0368820 A1* | 12/2014 | Sugasawa | G01N 15/0211 |
| | | | 356/336 |
| 2016/0003730 A1 | 1/2016 | Schreuder et al. | |
| 2016/0077218 A1 | 3/2016 | Loi et al. | |
| 2016/0266029 A1 | 9/2016 | Schreuder et al. | |
| 2020/0033244 A1 | 1/2020 | Boutami et al. | |

* cited by examiner

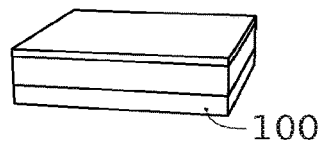
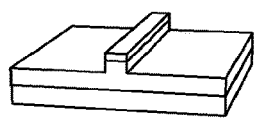
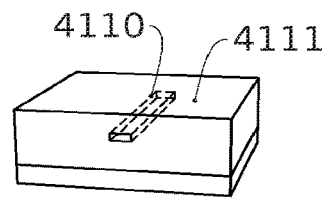
FIG. 5A　　　FIG. 5B　　　FIG. 5C
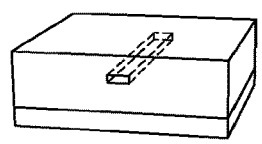
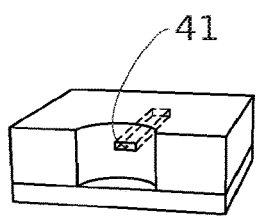
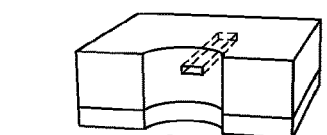
FIG. 5D　　　FIG. 5E　　　FIG. 5F
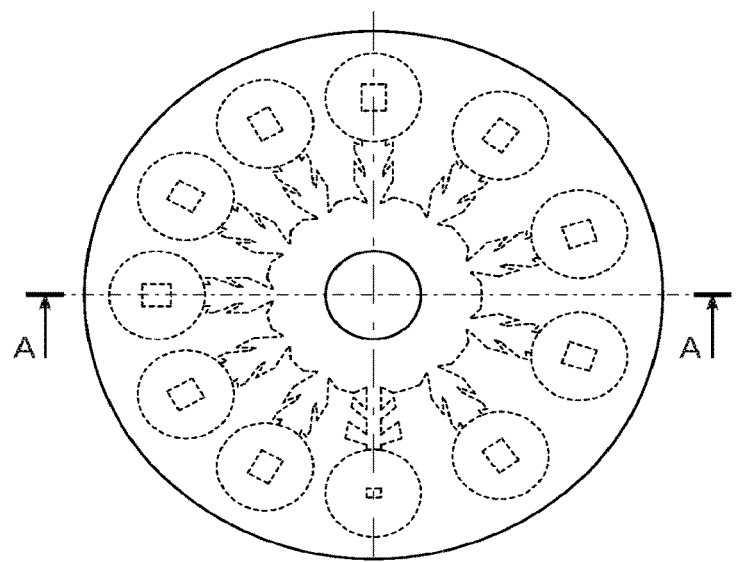
FIG. 6A
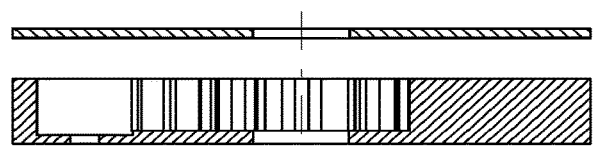
COUPE A-A
FIG. 6B

OPTICAL PARTICLE DETECTOR

TECHNICAL FIELD

The present invention relates to the field of the optical detection of particles in general and more particularly particles of micrometric or even nanometric size. It also relates to the angular analysis of the diffusion of one or more particles.

It will find a particularly advantageous, but non-limitative, application in the monitoring of air quality, the detection of microbiological species, fire detection and the detection of explosive powder.

PRIOR ART

Particles are microscopic objects, solids, liquids or wetted solids in suspension in air. The sizes thereof vary from a few tens of nanometres to a few tens of micrometres. These particles come from varied sources such as forest fires, construction sites, industrial sites, motorised vehicles, etc.

When the concentration of these particles exceeds a certain threshold, they have a harmful impact on the environment and/or health. Thus states have fixed maximum concentration thresholds. For example, the European Union allows maximum concentrations of 50 µg/m$^3$ for particles with a size of between 10 µm and 2.5 µm and 25 µg/m$^3$ for particles with a size below 2.5 µm.

It is therefore necessary to detect with precision the presence and the concentration of these particles per size range.

Various particle detection methods exist, such as methods of detection by gravimetry, ionisation and beta attenuation, methods of detection by measurement of aerodynamic mobility or electrical mobility, and optical detection methods.

The latter are advantageously simpler to implement, and more widespread. The optical detection of particles is generally done by means of a device comprising a light source that illuminates a channel through which the particles to be detected pass, and at least one photodetector.

If particles are present in the illuminated zone, these will absorb part of the light that comes from the source and will divert another part of this light out of the main propagation direction, in accordance with the phenomenon of diffusion.

A first optical detection method, referred to as obscuration measurement, therefore consists of measuring the absorption of light through a cloud of particles or an accumulation of particles. This measurement makes it possible to determine the concentration of the particles using the Beer-Lambert law if in principle the composition of the cloud of particles is known.

A second method consists of analysing the light diffused outside the optical axis. Angular analysis of the diffused light, using the recording of an angular-radiation diagram, makes it possible to determine the shape, size, optical index and concentration of the particles. For example, the size, the refractive index and the concentration of particles can be determined from light-diffusion theories, for example the Mie theory (Ref: Bohren and Huffmann, Absorption and Scattering of Light by Small Particles, Wiley and Sons, 1983). To perform this angular analysis, it is possible to use for example a device comprising a goniometer consisting of a photodetector mounted on a rotary arm, or a device comprising a discrete assembly of photodetectors distributed outside the optical axis.

An angular analysis by a device comprising a goniometer has the drawbacks of being very complex, very expensive and not very robust. Thus it cannot be easily transported. Moreover, it cannot be envisaged for equipping alarm or measuring systems at low cost. However, for example for the field of fire detection in dwellings or for the field of air-quality monitoring, it is essential to propose solutions where the costs are low and the robustness is high.

The document FR 3062209 A1 describes another solution for performing an angular analysis. This solution is based on a device comprising a discrete assembly of photodetectors forming a matrix and reflective surfaces for projecting onto the matrix the image of the radiation diffused by the particles. In practice, it turns out that this solution generates angular fuzziness on the angular radiation diagram.

This solution also generates measurement noise on the angular diagram.

The angular analysis performed by such a detector is therefore noisy and of low resolution.

It is therefore difficult with this type of solution to obtain sufficiently precise and complete information on the particles.

The objective of the present invention is to at least partly overcome the drawbacks cited above.

One object of the present invention is an optical particle detector making it possible to obtain an angular radiation diagram while limiting angular fuzziness.

Another object of the present invention is an optical particle detector making it possible to obtain an angular radiation diagram while limiting the measurement noise.

SUMMARY

The present invention relates to an optical particle detector comprising at least:
- a channel intended to receive a fluid comprising at least one particle and to receive at least one incident light ray,
- a detection system comprising a plurality of photodetectors, each photodetector being able to receive light rays coming from the channel and diffused by the at least one particle.

Advantageously, the detector further comprises an angular filtering system comprising a plurality of angular filtering devices each associated with a photodetector, each angular filtering device being configured to angularly filter the light rays coming from the channel before reception thereof by the photodetector with which it is associated.

Each photodetector thus benefits from an angular filtering device that is particular to it.

Each photodetector receives only part of the light rays coming from the channel, this part being included in a region delimited by limit angles of incidence of the light rays, defined by the angular filtering device of the photodetector.

This makes it possible to prevent light rays having an angle of incidence greater than the limit angles of incidence defined by the angular filtering device from being detected by the photodetector.

This region delimited by the limit angles of incidence corresponds to the collection cone of the angular filtering device.

This collection cone 40 and the principle of angular filtering is illustrated in FIG. 1.

In the context of the development of the present invention, it has turned out that the angular fuzziness that is found in the detectors of the prior art is in particular due to parasitic diffusions that are generated by the presence of a plurality of particles 10, 10' in the channel 1 or by the variation in position of a diffusing particle in the channel 1.

This is because, with the detectors of the prior art, if any one photodetector 33 simultaneously receives the diffused light rays ii and iii respectively from the particles 10 and 10' present at the same instant in the channel 1, this photodetector 33 is then not able to supply precise information for only one of the particles, the particle 10 for example.

With the detector according to the invention, the light ray iii from the particle 10' remains outside the collection cone 40 of the angular filtering device 431 associated with the photodetector 33. This light ray iii is therefore never detected by the photodetector 33, although the particle 10' is present in the channel. It is then possible to analyse, with significantly improved precision, the particle 10 the light ray ii from which enters the collection cone 40 and reaches the photodetector 33.

The angular fuzziness of the photodetector is advantageously limited by virtue of the angular filtering device of the present invention.

As indicated above, the angular fuzziness found with the detectors of the prior art may also result from the variation in position of a diffusing particle in the channel 1.

In this case, a particle 10 diffuses, when it is situated in an initial position, for example a light ray ii and a light ray iii. The light ray ii is included in the collection cone 40 of the angular filtering device 431 associated with the photodetector 33. It is therefore detected by the photodetector 33. The light ray iii is outside the collection cone 40 of the angular filtering device 431 associated with the photodetector 33. It is not detected by the photodetector 33.

When the particle 10 moves into a particle position 10', the known photodetector solutions lead to a detection of the light ray iii by the photodetector 33. This first parasitic detection source causes angular fuzziness in the angular analysis of the rays diffused by the particle 10, 10'.

With the present invention, the light ray iii advantageously remains outside the collection cone 40 of the angular filtering device 431 associated with the photodetector 33. The light ray iii is therefore never detected by the photodetector 33, although the particle has moved. The angular fuzziness of the photodetector is advantageously limited by virtue of the angular filtering device of the present invention.

Another parasitic detection source comes from light rays iv diffused indirectly, for example by an edge of the channel 1 or by a protective layer, for example an encapsulation of the photodetectors. These indirect light rays iv are also detected by the photodetectors of the detectors of the prior art. They then generate a measurement noise in the angular analysis of the rays diffused by the particle 10.

With the present invention, the light rays iv advantageously remain outside the collection cone 40 of the angular filtering device 431 associated with the photodetector 33. These light rays iv are therefore never detected by the photodetector 33. The measurement noise of the photodetector is advantageously limited by virtue of the angular filtering device of the present invention.

Thus the present invention has a particular advantage for photodetectors in which a channel or an encapsulation layer inevitably generates parasitic diffusions.

With the detector according to the invention, the light rays coming from the channel are advantageously collected selectively by an angular filtering device, according to their angles of incidence and the position of their emission or re-emission source, provided that they are situated in the collection cone of the angular filtering device in question.

Advantageously but only optionally, the detector according to the invention may have at least some of the optional features stated below, which may optionally be used in association or alternatively.

Each angular filtering device preferably comprises an optical entry having a numerical aperture of less than 0.3, preferably less than 0.2, and preferably around 0.1.

The numerical aperture is proportional to the aperture half-angle $\gamma$, corresponding to the limit angle of incidence, relative to the optical axis of the entry of the angular filtering device in question, beyond which a light ray is no longer collected by this entry.

Thus the diffused light rays having a direction of propagation forming an angle of incidence, relative to the optical axis of the entry in question, greater than $\gamma$ are rejected by said entry.

For a fluid such as air having a refractive index of approximately 1, a numerical aperture of less than 0.3 corresponds to an aperture half-angle $\gamma$ less than approximately 17°.

An angular filtering system comprising such angular filtering devices therefore advantageously makes it possible to limit, or even eliminate, parasitic diffusion, that is to say diffusion comprising the rays iv indirectly diffused by elements other than the particle or particles.

Moreover, the collection at an entry of a ray directly diffused by a particle means that this particle is situated in the collection cone defined by the numerical aperture of said entry of the angular filtering device.

The rays iii directly diffused by a particle situated outside this collection cone are not collected by this entry.

Such an angular filtering system therefore advantageously makes it possible to limit angular fuzziness.

The present invention also relates to a system comprising such a detector, the system being taken from among:
  a fire alarm system,
  a fire detection system,
  a system for analysing the quality of a fluid such as air or water,
  a pollution alarm system,
  an explosive-powder detection system,
  a microbiological-species detection system.

The present invention also relates to a method for manufacturing such a particle detector, comprising at least the following steps:
  providing a substrate,
  defining, on one face of the substrate, the channel and the angular filtering devices surrounding the channel,
  forming the channel through the substrate in order to provide a passage for the fluid,
  forming the angular filtering devices on the face of the substrate,
  associating a photodetector with each angular filtering device.

BRIEF DESCRIPTION OF THE FIGURES

The aims, objects, features and advantages of the invention will emerge more clearly from the detailed description of the embodiments thereof that are illustrated by the following accompanying drawings, wherein:

FIGS. 5A-5F illustrate steps of a manufacturing method that may be suitable for example for producing a detector according to the embodiments illustrated in FIGS. 1 to 3A. FIG. 5A illustrates a deposition of layers intended to form at least one waveguide. FIG. 5B illustrates a formation of at least one waveguide by lithography/etching techniques. FIG. 5C illustrates a step of encapsulation of at least one waveguide. FIG. 5D illustrates a step of annealing at least one waveguide.

FIG. 5E illustrates a step of superficial etching of a channel. FIG. 5F illustrates a step of deep etching of a channel.

FIG. 6A illustrates an embodiment in a semicircle of a detector according to the invention.

FIG. 6B is a cross section of FIG. 6A along A-A.

Figure 1:
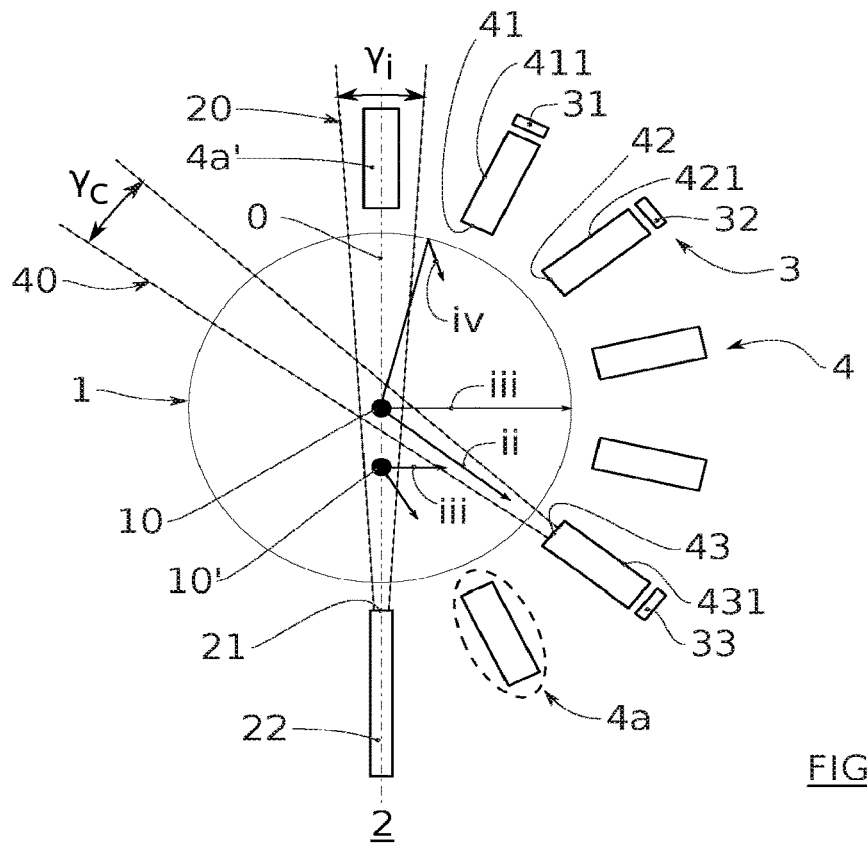
FIG. 1 is an outline diagram, in plan view, illustrating a particle illuminated by an illumination cone and diffusing in a collection cone of an angular filtering system according to one embodiment of a detector according to the invention.

The drawings are given by way of examples and are not limitative of the invention. These drawings are schematic representations and are not necessarily to the scale of the practical application. In particular, the relative dimensions of the various layers, patterns, cavity, photodetectors and other structures do not represent reality.

DETAILED DESCRIPTION

The numerical aperture is a characteristic of an optical system, generally denoted NA according to English terminology, standing for "Numerical Aperture".

It is defined by $NA = n_0 \cdot \sin i_0$, where $n_0$ is the refractive index in the observation medium, and $i_0$ is the angle between the optical axis of the optical system and the radius most inclined with respect to the optical axis, which emerges from or enters the optical system. This angle is referred to as the aperture half angle. The aperture angle will be denoted $\gamma = 2 \cdot i_0$.

In the case of the light sources, it appears that light emitting diodes LED, which are not very directive, have numerical apertures significantly greater than laser diodes, which are very directive.

In the case of a guide structure such as an optical fibre or a waveguide comprising a core of index $n_c$ and a sheath of index $n_0$, the numerical aperture is expressed in accordance with the formula:

$$NA = \sin i_0 = \sqrt{n_c^2 - n_g^2}$$

independently of the refractive index $n_0$ of the external medium. NA is a characteristic particular to the guide structure. It appears that, by reducing the index contrast, that is to say the difference between these two indices $n_c$ and $n_g$, the numerical aperture NA decreases.

In the case of a guide structure, the collection cone of the guide structure is dependent on the numerical aperture.

Collection cone means a beam of light rays, in particular diffused light rays, admissible by the optical system. The collection cone does not necessarily have a circular base or axial symmetry. The collection cone may for example have an elliptical base or a rectangular base.

In the context of the present invention, the term "particle" or the equivalents thereof is defined as a constituent of a physical system considered as elementary with respect to the properties studied.

The term particles designates in particular an object that is solid, liquid or wetted solid in suspension in air and the size of which is microscopic. For example, a particle is an element of matter the largest dimension of which is less than a few millimetres ($10^{-3}$ metres), preferably less than one millimetre, and preferably less than a few tens of micrometers ($10^{-6}$ metres) and preferably less than one micrometre, or even around a nanometre ($10^{-9}$ m). More generally, particles have a size greater than 40 Å ($10^{-10}$ m) and are therefore considered to be optically continuous. Generally, it is a case of objects composed of matter the dimensions of which are small compared with the dimensions of the cavity or channel in which the particles circulate.

"Size" or "diameter" of a particle means the maximum distance between two points on the particle. Typically, a particle is assimilated to an object with a spherical shape, and its size therefore corresponds to the diameter of the sphere.

A substrate, a waveguide, a film or a layer "based" on a material A means a substrate, a waveguide, a film or a layer comprising this material layer solely or this material A and optionally other materials, for example doping elements or alloy elements. Thus, if a waveguide is designated as being "based on polymers", this means that it may be formed solely from polymers or from polymers and optionally other materials, for example an inorganic oxide.

In the context of the present invention, the terms "on", "surmounts", "covers" or "underlying" or the equivalents thereof do not mean "in contact with". Thus, for example, the deposition of a first layer on a second layer does not necessarily mean that the two layers are directly in contact with one another but means that the first layer at least partially covers the second layer while being either directly in contact therewith or being separated therefrom by at least one other layer or at least one other element.

Unless specifically indicated to the contrary, technical features described in detail for a given embodiment may be combined with the technical features described in the context of other embodiments described by way of example and non-limitatively.

Hereinafter, the term "absorption" or the equivalents thereof refers to the phenomenon by means of which the energy of an electromagnetic wave is transformed into another form of energy, for example in the form of heat. In the present description, a material is considered to be absorbent provided that it absorbs at least 50% of a light radiation, preferably at least 75% and advantageously at least 90%. It can be characterised by an absorption factor of between 0 and 1.

Hereinafter, the term "diffusion" or the equivalents thereof refers to the phenomenon by which a propagation medium produces a distribution, in numerous directions, of the energy of an electromagnetic wave, light for example.

Hereinafter, the term "reflection" or the equivalents thereof refers to the phenomenon of re-emission from an element or a surface of an incident light radiation. In the present description, an element is considered to be reflective provided that it re-emits at least a portion of an incident light radiation, this portion being greater than or equal to 50%. It can be characterised by a reflection factor of between 0 and 1.

The terms "substantially", "approximately" and "of the order of" signify "to within 10%" or, when it is a case of an angular orientation, "to within 5°". Thus a direction substantially normal to a plane signifies a direction having an angle of 90°±5° with respect to the plane.

Before beginning a detailed review of embodiments of the invention, optional features, which may optionally be used in association or alternatively, are stated below:

According to one example, each angular filtering device comprises an optical entry, the optical entry having a numerical aperture smaller than a numerical aperture of the photodetector with which the angular filtering device is associated.

According to one example, the angular filtering device is configured to define a collection cone at its optical entry, each connection cone having an aperture angle $\gamma_c$ of less than 35°, preferably less than 25°, and preferably between 15° and 10°, so as to collect diffused light rays having propagation directions having angles of incidence, in relation to an optical axis of the optical entry in question, of less than 17.5°, preferably less than 12.5°, and preferably between 7.5° and 5°.

According to one example, the channel is cylindrical and the optical entries are distributed at least partly around the channel, along at least a portion of at least one circle, preferably along at least a complete circle, the at least one circle preferably being centred on an axis of the channel.

According to one example, the photodetectors are disposed along at least two concentric circles, in alternation. This embodiment has the advantage of being compact.

According to one example, the plurality of photodetectors comprises at least 12 photodetectors.

According to one example, the optical entries are distributed along a semicircle.

According to one example, the photodetectors are distributed along a semicircle.

According to one example, the photodetectors are distributed along a linear array.

According to one example, each optical entry has an optical axis matching with a radius of the cylinder forming the channel.

According to one example, the angular filtering device comprises, between the entry thereof and the photodetector that is associated therewith, an optical guide structure from among an optical fibre, a waveguide, a lens or a light trap.

According to one example, the photodetectors comprise photodetection surfaces disposed so as to be situated in a plane transverse to a longitudinal axis of the channel, the detector further comprising at least one optical integration structure configured to transmit the diffused light rays collected at an optical entry, as far as the photodetection surface of the photodetector associated with the optical entry in question, said optical integration structure being for example an integrating sphere, an integrating washer, or a prism. This embodiment has the advantage of affording easy integration of the photodetectors when the detector is produced by the conventional microelectronic techniques, in particular by planar techniques.

According to one example, the channel is cylindrical and the optical entries are distributed around the channel on axes extending the radii of the cylinder, two successive axes being separated by a distribution angle θ of between 15° and 45°, preferably around 30°.

According to one example, the distribution angle θ of the optical entries around the channel is constant. For example, the distribution angle θ of the optical entries around the channel is constant along the detection circle or circles. This makes it possible to perform a symmetrical angular sampling. Thus the optical entries are distributed symmetrically around the axis of the channel. According to an alternative embodiment, the distribution angle θ of the optical entries around the channel is not constant. It varies around the channel. Typically, it varies along the circle or circles on which the optical entries are positioned. Thus the optical entries are distributed non-symmetrically around the axis of the channel. This makes it possible to increase the angular resolution of the detector.

According to one example, a first part of the optical entries are distributed over a first half of a circle and have a first distribution angle θ1, for example around 30°, and a second part of the optical entries are distributed over a second half of a circle and have a second distribution angle θ2 different from θ1, for example around 36°, so as to perform a non-redundant sampling of the diffused light rays.

According to one example, the detector further comprises, for at least some filtering devices, an optical structure intermediate between the channel and the optical entry, the intermediate optical structure being configured to reduce the divergence of the collection cone and/or to broaden a cross section of the collection cone of the optical entry, said intermediate optical structure being for example taken from a microlens and a microbead.

According to one example, the light source is isotropic and the detector comprises a device for forming an incident beam associated with the source and having an optical exit, said device for forming an incident beam being configured to form, at the optical exit, a cluster of incident light rays (i) having an aperture angle of less than 30°, preferably less than 20°, and preferably around 10°, said device for forming an incident beam preferably comprising one from among an optical fibre, a waveguide, a lens and a light trap.

According to one example, the detector has a principal extension dimension of less than 10 mm, preferably around 5 mm, the principal extension dimension preferably being taken in a direction transverse to a longitudinal axis of the channel.

According to one example, the angular filtering system comprises a plurality of light traps disposed around the channel, each light trap in this plurality of light traps being configured to transmit light rays in a beam with small divergence, having for example a divergence angle of less than 15°.

According to one example, each light trap comprises a principal optical axis along which the light rays having a divergence angle relative to the optical axis of less than 15° are transmitted, and absorbent branches on either side of the principle optical axis in which the light rays having a divergence angle relative to the optical axis greater than 15° are absorbed.

According to one example embodiment of the method, the angular filtering devices are light traps formed by etching of the substrate as from the face of the substrate.

According to one example embodiment of the method, the method for manufacturing the detector further comprises the formation of an optical integration structure configured to transmit the light rays from the angular filtering device to a photodetection surface of the photodetector associated with the angular filtering device in question, said photodetection surface extending mainly along planes parallel to the face of the substrate, and the optical integration structure being for example an integrating washer etched as from the face of the substrate.

According to one example embodiment of the method, the photodetectors are disposed on a linear array, and the linear array of photodetectors is associated with the angular filtering devices.

The present invention finds a preferential field of application in the detection of particles of various sizes, preferably in the microscopic or even nanometric particle range. For example, the present invention can serve for the detection of particles issuing from fumes, explosive powder, polluting particles, dust particles, allergenic particles such as pollens or fungus spores, or carcinogenic particles, or biological particles such as bacteria, viruses or exosomes.

The present invention applies to any type of particle conveyed by a fluid, whether the latter be liquid and/or gaseous.

The fluid present or flowing in the channel is for example air. Such is the case with detectors integrated in the following systems: a fire alarm system, a fire detection system, an explosive-powder detection system, a system for analysing the quality of a fluid such as air, or a pollution alarm system.

Alternatively, the fluid may be a liquid such as water. Such is the case with detectors integrated in systems for detecting microbiological species.

The present invention aims in particular to make angularly resolved diffusion measurements of one or more particles, in a detector manufactured by means of conventional micromanufacturing technologies.

A first simplified example of a detector according to the invention will now be described with reference to FIG. 1, in order to understand the operating principle thereof.

As illustrated in this diagram, the detector comprises a channel 1 in which a fluid comprising at least one particle 10 can flow, and a detection system 3 comprising a plurality of photodetectors 31, 32, 33 intended to collect diffused light rays ii. This plurality of photodetectors may comprise at least seven photodetectors, preferably at least twelve photodetectors, and preferably a number of photodetectors greater than twelve, so that the detector can perform a sufficiently complete angular sampling. The angular resolution of the detector can be increased by increasing the number of photodetectors.

The detector is coupled to an optical source 2. The source 2 is preferably distinct from the detector. This makes it possible to change or manufacture the source independently of the detector.

Advantageously, the detector further comprises an angular filtering system 4 configured to filter the collection of the diffused light rays ii at only certain diffusion angles. Such a system 4 makes it possible to reduce the measurement noise due to the parasitic diffusions that do not directly come from the particle 10. Such a system 4 also makes it possible to reduce the angular fuzziness generated by the movement of the particle 10, 10'. This system 4 also makes it possible to reduce the angular fuzziness generated by the diffusion on any one photodetector, for example the photodetector 33, of rays diffused simultaneously by a plurality of particles 10, 10' present in the channel (the references 10, 10' mean either two different positions of the same particle, or two distinct particles, for reasons of concision).

The structural elements for maintaining at a distance the channel 1, the source 2, the detection system 3 and the angular filtering system 4 are not illustrated on this outline diagram.

These elements are for example an annulus, a barrel or a support plate hollowed at the centre thereof enabling the fluid to flow in the channel 1.

In this first example and in the following examples, the channel 1 is preferably cylindrical. The circulation of the fluid mainly takes place along the longitudinal axis of this channel. In FIG. 1, this axis is perpendicular to the plane of the sheet. This channel may have a transverse dimension, for example a diameter, of between 100 μm and 3 mm.

The emission of the incident light rays i and the collection of the diffused light rays ii preferably take place in a plane transverse to the longitudinal axis of this channel 1.

The emission of the incident light rays i takes place at an optical exit 21 associated with a light source 2.

The source 2 may be associated with a device 22 for forming an incident beam, configured to transmit incident light rays i included in an illumination cone 20 extending from the optical axis 21.

This device 22 for forming an incident beam may be a guide structure such as a waveguide, an optical fibre, a light trap or a microlens system for example.

The optical axis 21 therefore has a numerical aperture NAi making it possible to emit only the incident light rays i included in its illumination cone 20.

The numerical aperture NAi is less than 0.3, preferably less than 0.2, and preferentially around 0.1. These range of values of NAi correspond approximately to aperture angles γi of the illumination cone 20 of less than 30°, preferably less than 20°, and preferentially around 10°.

According to one embodiment, the source 2 is a laser diode making it possible to directly obtain the required directivity and divergence for the incident light rays i.

According to another embodiment, the source 2 is an LED diode associated with a guide structure making it possible to indirectly obtain the directivity and the divergence required for the incident light rays i.

The illumination cone 20 may therefore be formed directly from a laser diode or indirectly from an LED.

According to an alternative embodiment, the source 2 is the sun.

Figure 7A:
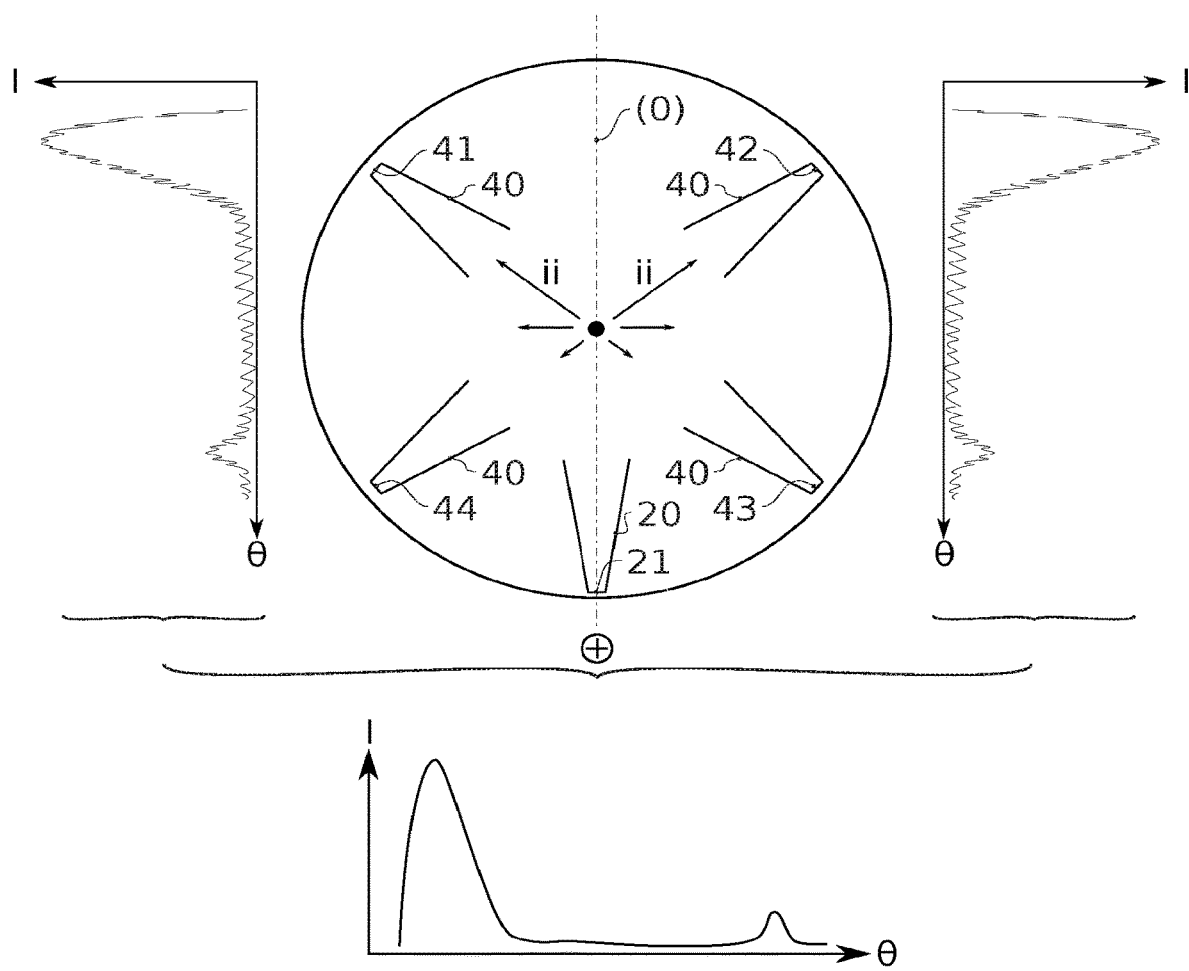
FIG. 7A illustrates schematically a symmetrical angular sampling performed by a detector according to an embodiment of the invention.
Figure 7B:
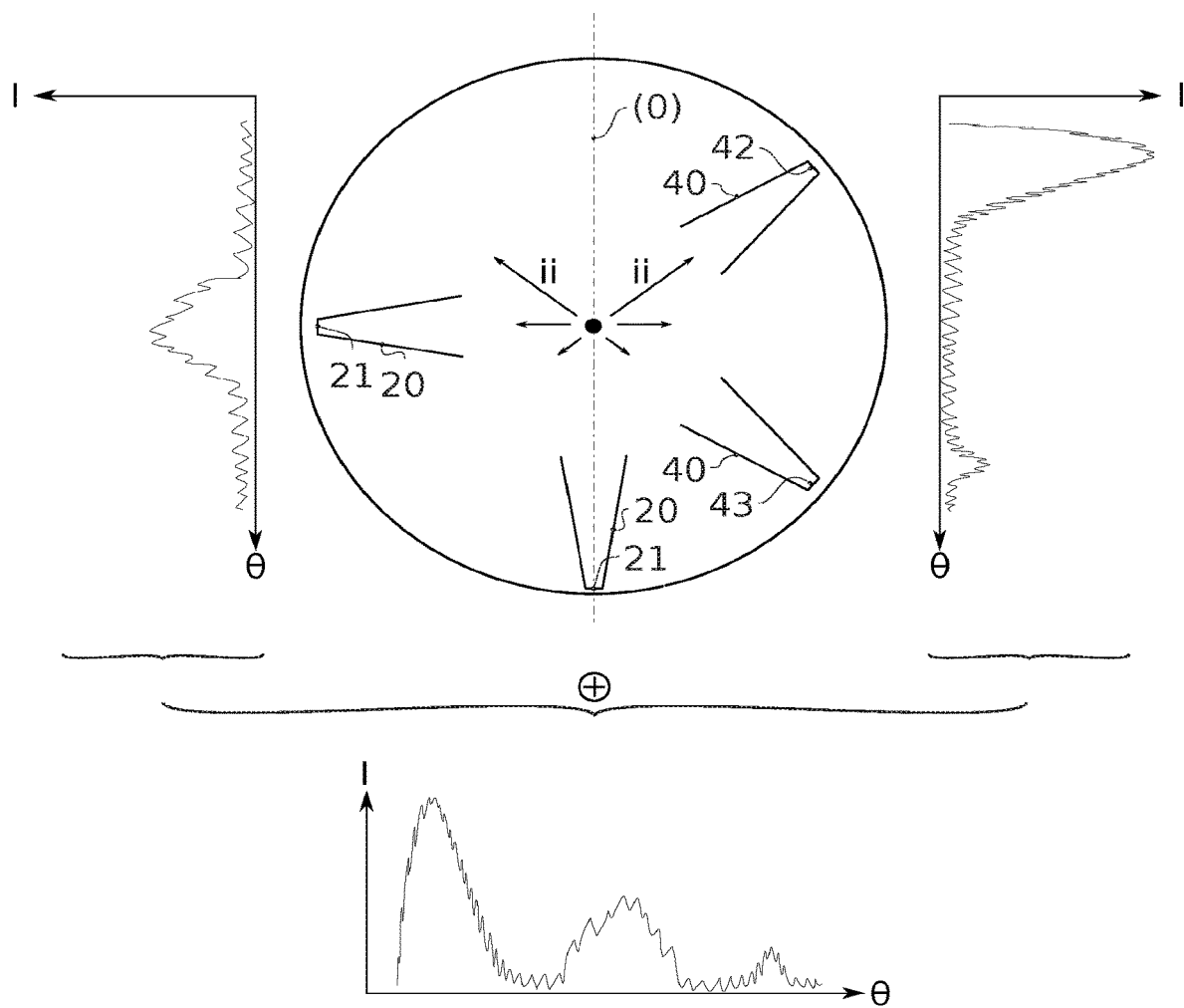
FIG. 7B illustrates schematically an asymmetric angular sampling performed by a detector according to an embodiment of the invention.

A particle present in the channel 1 passing through the illumination cone 20 will generate diffused light rays ii. These diffused light rays ii are re-emitted by the particle 10 symmetrically on each side of the optical axis (○) of the illumination cone 20, also referred to as the optical axis of the source 2, as depicted in FIGS. 7A and 7B.

The collection of the diffused light rays ii advantageously takes place at the optical entries 41, 42, 43 of the angular filtering devices 4a.

As will be illustrated in detail hereinafter, each angular filtering device 4a is associated with a photodetector 31, 32, 33 and makes it possible to angularly filter the light rays arriving at this photodetector 31, 32, 33.

Hereinafter, an angular filtering device 4a, 4b, 4c, 4d is preferably formed by an optical entry 4x and a guide structure 4xy.

The optical entries 41, 42, 43 of these angular filtering devices are disposed around the channel 1, so as to collect diffused light rays ii having various angles of incidence.

They may be disposed on a semicircle, from the source 2 as far as an optical entry diametrically opposed to the source 2, opposite the source 2, facing the source 2.

They may alternatively be disposed on a complete circle. They may also be disposed on two concentric circles, in alternation or staggered, as illustrated hereinafter by other example embodiments. These choices can depend on the manufacturing costs, the space requirement and the angular resolution required for the detector.

The optical entries may delimit partly at least the channel 1, for example directly at a wall of the channel 1.

Alternatively, they may be separated by the wall of the channel 1. In this case, they may be covered by a protective or encapsulation layer so as to prevent soiling of said optical entries.

The detector preferably comprises a filtering device 4a' the optical entry of which is aligned on the optical axis of the source 2, facing the source 2. The photodetector associated with such an optical entry advantageously makes it possible to make measurements of an absorption of the particles and/or checks on drift of the source 2. This optical entry may also make it possible to collect part of the light rays not used for the angular analysis, for example incident light rays i not diffused by the particle 10. This collected particle may then be reinjected into the channel, either so as to maintain good luminosity of the illumination cone 20, or so as to form another illumination cone, for example at a lower stage of the channel. This makes it possible to limit the optical losses of the illumination cone 20. This ultimately makes it possible to benefit from a major part of the light emitted by the source 2 for purposes of analysis.

The optical entries 41, 42, 43 preferably transmit the diffused light rays ii to the photodetectors 31, 32, 33 by means of guide structures.

These guide structures may for example be waveguides 411, 421, 431 as illustrated in FIG. 1. As will be described in detail with reference to FIGS. 2 to 4A, these guide structures may also be optical fibres 412, 422, 432, microlens systems 413 or light traps 414, 424, 434.

Such a guide structure is configured to transmit diffused light rays ii included in the collection cone 40 extending from the optical entry associated with said guide structure.

Each optical entry 41, 42, 43 therefore has a numerical aperture NAc1, NAc2, NAc3, preferably the same numerical aperture NAc=NAc1=NAc2=NAc3, making it possible to collect only the diffused light rays ii included in its collection cone 40.

The numerical aperture NAc is less than 0.3, preferably less than 0.2, and preferentially around 0.1.

These ranges of value of NAc correspond approximately to aperture angles γc of the collection cone 40 of less than 30°, preferably less than 20°, and preferentially around 10°.

In order to improve the precision of angular analysis of the detector, it is preferable to reduce the numerical aperture NAc of the guide structure. In order to improve the amplitude of the light signal collected, it is preferable to increase the numerical aperture NAc of the guide structure. According to the required performances, a person skilled in the art will know how to determine the suitable numerical aperture NAc, and to produce the guide structures having such a numerical aperture NAc.

The number of optical entries and/or of guide structures disposed around the channel 1 is determined by the required angular sampling. For example, for a distribution of the optical entries and/or of the guide structures over a semicircle, this number is preferably at least $\pi/2 \cdot \arcsin(NAc)$.

As illustrated in FIG. 7A, for a symmetrical distribution of the optical entries vis-à-vis the optical axis (O), the angular sampling performed by the detector is symmetrical. The angular sampling is redundant and may be averaged. The noise affecting the angular analysis of the detector can thus be reduced.

As illustrated in FIG. 7B, for an asymmetric distribution of the optical entries vis-à-vis the optical axis (O), the angular sampling performed by the detector is asymmetric. The angular sampling is non-redundant. The angular resolution of the detector can thus be increased.

The various possibilities of distribution of the optical entries around the channel 1 are compatible with all the embodiments described hereinafter. For reasons of concision, each of the embodiments illustrated hereinafter is described for a type of distribution of the optical entries only, without this being limitative.

The intersection of the illumination cone 20 and a collection cone 40 makes it possible to define a useful volume V as illustrated in FIG. 1. The superimposition of the useful volumes V makes it possible to define an analysis volume in which the diffusion of the particle 10 can be analysed angularly by the detector.

By reducing the aperture angle of the illumination and/or collection cones, the analysis volume is advantageously reduced. This makes it possible to perform a spatial filtering for the position of the particles. This makes it possible to limit the angular fuzziness during the angular analysis of a stream of particles.

According to a first embodiment illustrated in FIG. 1, the guide structures associated with the optical entries 41, 42, 43 of the angular filtering devices 4a are linear waveguides 411, 421, 431.

These linear waveguides guide the diffused light rays ii collected to the corresponding optical entries, mainly along their respective longitudinal axes.

The longitudinal axes of these linear waveguides coincide with radiis of the cylinder forming the channel 1.

The photodetectors 31, 32, 33 (for reasons of clarity only some of the photodetectors are depicted in FIG. 1) are positioned in line with the various longitudinal axes, preferably so that the photodetection surfaces thereof are normal to the longitudinal axes. The photodetectors may be coupled to their respective waveguides by direct coupling.

For such a detector, the angular resolution of the detector can be assimilated to $\pm \arcsin(NA)$.

The efficacy of angular detection of such a detector is optimised.

Figure 2:
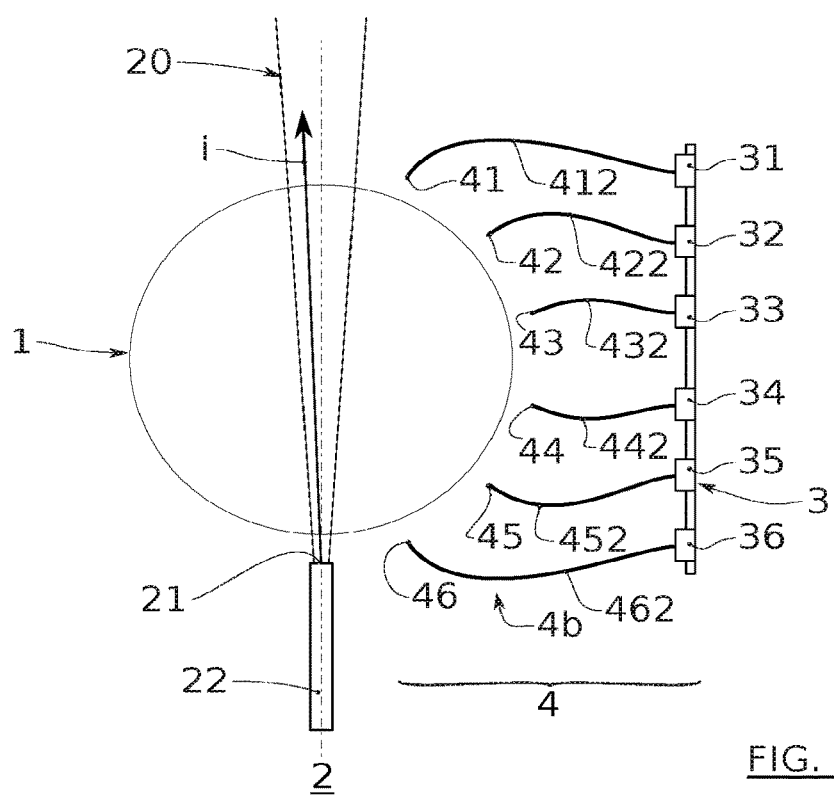
FIG. 2 is an outline diagram, in plan view, of an embodiment alternative to the one illustrated in FIG. 1.

According to a second embodiment illustrated schematically in FIG. 2, the guide structures associated with the optical entries 41, 42, 43 of the angular filtering devices 4b are optical fibres 412, 422, 432.

These optical fibres 412, 422, 432 guide the diffused light rays ii collected to the corresponding optical entries 41, 42, 43 in particular along curved paths.

The optical axes of the entries 41, 42, 43 of the optical fibres 412, 422, 432 coincide with radii of the cylinder forming the channel 1.

The photodetectors 31, 32, 33 are positioned at the exit of the optical fibres 412, 422, 432, preferably on the same linear array, or on the same matrix of photodetectors.

This makes it possible to simplify the integration of the photodetectors in the detector. The linear array of photodetectors may be coupled to the optical fibres so that the photodetection surfaces of the photodetectors are normal to the optical axes at the exit from the fibres. Alternatively, the linear array of photodetectors may be coupled to the optical fibres by the edge, i.e. so that the photodetection surfaces of the photodetectors are parallel to the optical axes at the exit from the fibres.

In the latter case, the exit from the optical fibres may have an interface oriented at an internal total reflection angle so as to transmit the diffused light rays ii guided as far as the photodetection surfaces of the photodetectors.

Alternatively, a coupling grating may make it possible to extract the diffused light rays ii guided in the fibres, in order to transmit them to the photodetection surfaces of the photodetectors.

The photodetectors may be separated from the guide structures, so that there is no contact between the photodetection surfaces of the photodetectors and these guide structures.

The linear array of photodetectors of the detector can easily be changed. Maintenance of such a detector is consequently facilitated.

Figure 3A:
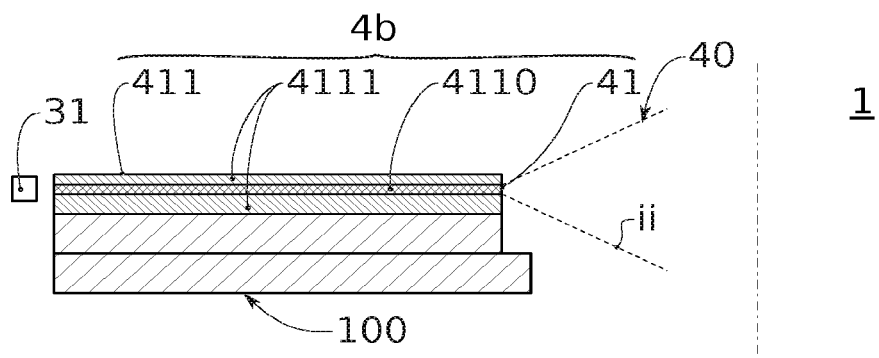
FIG. 3A illustrates schematically, in a view in cross section, an embodiment of an angular filtering device comprising a waveguide.
Figure 3B:
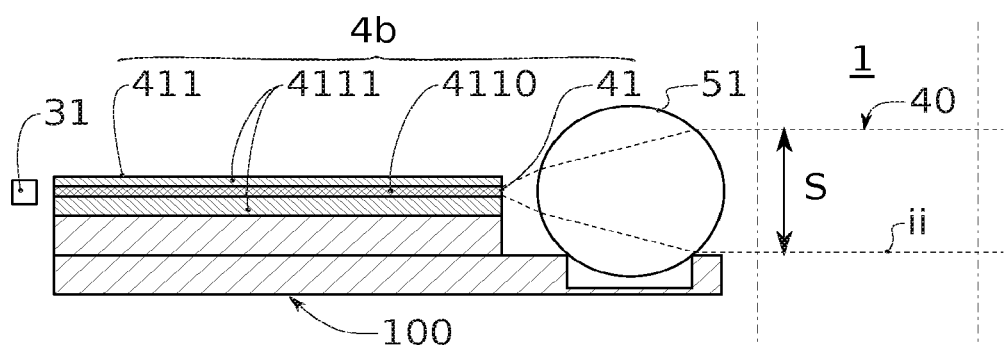
FIG. 3B illustrates schematically in a view in cross section, an embodiment of an angular filtering device comprising a waveguide associated with a microbead.
Figure 3C:
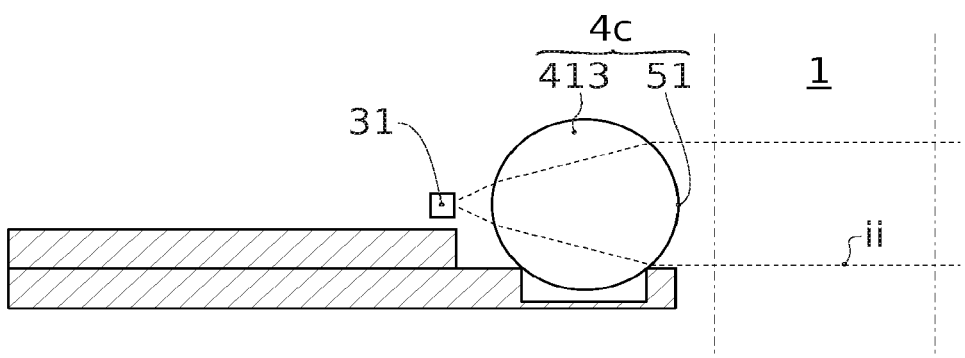
FIG. 3C illustrates schematically, in a view in cross section, an embodiment of an angular filtering device comprising a microbead.

FIGS. 3A, 3B, 3C illustrate filtering devices having various collection and/or guidance structures that can be associated with the photodetectors and/or with the light source 2.

FIG. 3A illustrates in longitudinal section a waveguide 411 comprising a core 4110 and a sheath 4111, mounted on a support 100. The diffused light rays ii coming from the channel 1 and included in the collection cone 40 are collected at the optical entry 41, guided by the waveguide 411 and transmitted to the photodetector 31.

Such a guide structure formed by a waveguide can easily be implemented by means of conventional micromanufacture technologies.

FIG. 3B illustrates in longitudinal section a waveguide 411 comprising a core 4110 and a sheath 4111, mounted on a support 100. The support 100 is configured to receive also an intermediate optical structure 51 between the channel 1 and the optical entry 41. This intermediate optical structure 51 preferably contributes to the shaping of the collection cone 40, for example so as to improve the angular resolution and/or the detection sensitivity associated with the optical entry in question.

This intermediate optical structure 51 can be configured so as to reduce the divergence of the collection cone 40, for example in the case of a waveguide with a high index contrast. It may also broaden an S section at the base of the collection cone 40, on the same side as the entry 41. A microbead 51, for example made from a transparent polymer, having a diameter of between 10 and 500 μm, may allow such a shaping of the collection cone 40.

FIG. 3C illustrates in longitudinal section a bead, also designated as microbead, mounted on a support 100, directly associated with a photodetector 31. This bead is directly configured to form at least partly the angular filtering device 4c. In this example illustrated in FIG. 3C, the bead forms by itself the angular filtering device 4c. This bead therefore has an optical entry 41 for connecting the diffused light rays ii included in the collection cone 40. It also makes it possible to transmit these diffused light rays ii to the photodetector 31.

Such a collection structure formed by a bead is advantageously inexpensive.

The optical entries associated with these collection and/or guide structures preferably have a collection cross-section S of a few tens of $\mu m^2$, typically around 40 $\mu m^2$ or even around 100 $\mu m^2$.

The description of FIGS. 3A-3C applies mutatis mutandis, in accordance with the principle of inverse light return, to the case of a light source 2, the photodetector 31 becoming the source 2, the entry 41 becoming the exit 21, the collection cone 40 becoming the illumination cone 20, and the diffused light rays ii becoming the incident light rays i. It is thus possible to focus the source beam.

FIGS. 5A to 5F describe schematically the production of a waveguide 411 of a detector according to the invention. This description can also relate to the production of an optical fibre. More generally, the principle illustrated in these FIGS. 5A to 5F may serve to produce all or part of a detector according to the embodiments illustrated in FIGS. 1 to 3B.

A support 100 made from a semiconductor material such as silicon is provided. It may be thinned in advance so as to keep a thickness of the support 100 of between 500 μm and 1 mm.

A first layer made from a first optical polymer is deposited, preferably over a thickness of between 5 μm and 50 μm, so as to form the bottom part of the sheath 4111 of the waveguide 411.

A second layer made from a second optical polymer is deposited, preferably over a thickness of between 5 μm and 25 μm, so as to constitute the core 4110 of the waveguide 411 (FIG. 5A).

This second optical polymer preferably has a refractive index greater than that of the first optical polymer, so as to obtain a confinement by contrast of indices of the light rays transmitted by the waveguide 411.

This second optical polymer is chosen so as to have a low index contrast with the first polymer. By thus minimising the index contrast, the numerical aperture of the waveguide is advantageously minimised.

The thicknesses of the core 4110 and sheath 4111 are preferably chosen so that the waveguide 411 with a low optical index contrast is configured so as to guide the light propagating in accordance with so-called extended optical modes, having for example transverse extension dimensions (with respect to the propagation axis, or with respect to the optical axis of the waveguide) of several micrometres.

The core pattern of the waveguide 411 is next defined and/or etched by conventional lithography and/or etching methods (FIG. 5B). According to one example, the second optical polymer constituting the core is a negative photosensitive optical resin of type SU-8 conventionally used in the microelectronic industry. The structuring of the core pattern of the waveguide can consequently take place solely by lithography, that is to say using an exposure step, preferably under UV radiation, followed by a development step, preferably with a liquid developer.

This pattern is next encapsulated by an encapsulation layer based on the first polymer so as to form the top part of the sheath 4111 of the waveguide 411, complementary to the bottom part (FIG. 5C). The top part preferably has a thickness substantially equal to the thickness of the bottom part. According to an alternative possibility, this encapsulation layer may comprise a third optical polymer having a refractive index close to or substantially equal to that of the first optical polymer.

The sheath 4111 is thus totally formed.

Preferably but optionally, an annealing step may be performed so as to cause a diffusion of the first and/or second optical polymer on the walls of the core 4110 (FIG. 5D). This diffusion advantageously improves the optical quality of the walls.

The channel 1 of the detector can next be etched through the sheath layers and/or the core 4110.

The channel 1 is etched so as to form the optical entry 41 of the waveguide 411 flush with said channel 1 (FIG. 5E).

The formation of the channel 1 is continued with a deep etching of the silicon support 100 (FIG. 5F).

This method advantageously makes it possible to produce a plurality of polymeric waveguides disposed in a base plane around a channel 1 inexpensively.

According to an alternative possibility, the waveguides may be based on ion-exchange doped glasses. According to another possibility, the waveguides may have a core based on SiON and a sheath based on $SiO_2$.

Figure 4A:
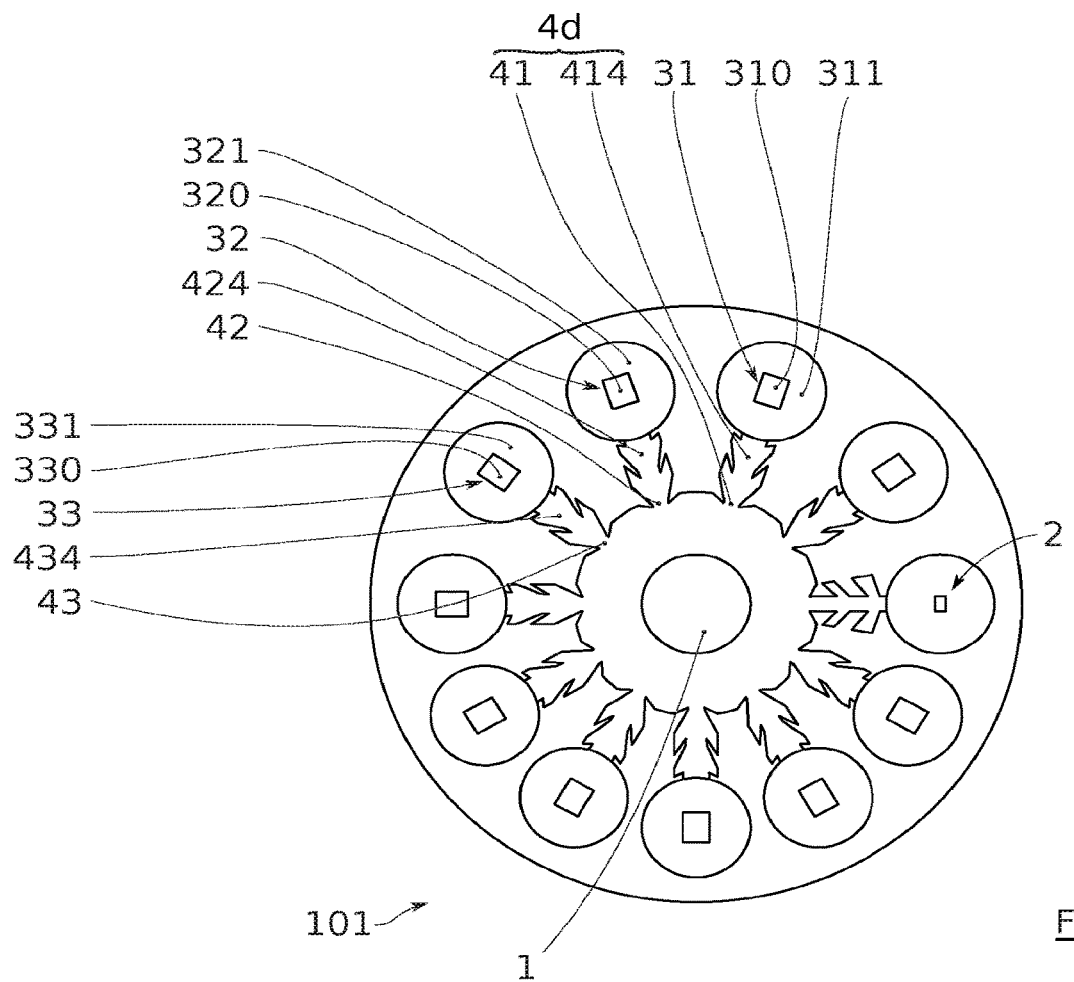
FIG. 4A illustrates, in plan view, an embodiment of a detector according to the invention, wherein the angular filtering system comprises light traps.

According to a third embodiment of the detector illustrated in FIGS. 4A to 4D, the detector is in the form of a barrel 101 extending over a base plane (FIG. 4A). This barrel is however not necessarily cylindrical.

This barrel 101 comprises a through central channel 1, preferably cylindrical, an optical exit 21 and a plurality of optical entries 41, 42, 43 disposed along a first circle, referred to as the collection circle, around and centred on the channel 1. The plane in which the barrel 101 mainly lies is preferably perpendicular to the longitudinal axis of the channel 1.

The barrel 101 further comprises a plurality of housings 311, 321, 331, preferably cylindrical, disposed along a second circle, referred to as the detection circle, with a diameter greater than the diameter of the collection circle. The detection circle is preferably centred on the channel 1. The detection and collection circles are preferably concentric.

The cylindrical housings 311, 321, 331 are intended to receive the light source 2 and the photodetectors 31, 32, 33.

The barrel 101 further comprises a plurality of light traps 414, 424, 434 disposed in a star, along radii of the detection circle.

This plurality of light traps forms the angular filtering system 4. Each light trap 414, 424, 434 has an optical entry 41, 42, 43 and forms, partly and preferably entirely, a filtering device 4d, as is illustrated in FIG. 4A.

A light trap is configured to transmit light rays in a small-divergence beam, having for example a divergence angle of less than 15°.

Such a light trap may comprise a principal optical axis along which the light rays having a divergence angle in relation to the optical axis of less than 15° are transmitted, and absorbent branches on either side of the principal optical axis in which the light rays having a divergence angle in relation to the optical axis greater than 15° are absorbed.

The absorbent branches are oriented in the direction of propagation of the light rays, forming an acute angle with the optical axis of the light trap. They are configured to absorb the light rays propagating therein. Only the light rays propagating mainly along the optical axis can thus pass through the light trap.

The cylindrical housing containing the light source 2 is connected to a "source" light trap having an optical exit 21 and having a principal axis oriented along a radius of the collection circle.

A cylindrical housing 311, 321, 331 containing a photodetector 31, 32, 33 is connected to a "photodetector" light trap 414, 424, 434 having an optical entry 41, 42, 43 and a principal axis oriented along a radius of the collection circle.

The absorbent branches of the "source" light trap and the absorbent branches of the "photodetector" light trap are oriented in opposite directions.

The light issuing from the exit 21 of the "source" light trap has a small divergence, whatever the divergence of the source 2 proper.

The light entering the optical entries 41, 42, 43 is filtered angularly by the "photodetector" light traps 414, 424, 434, so that only part of the diffused light rays ii included in the collection cone 40 of each of the optical entries 41, 42, 43 actually reaches the corresponding photodetectors 31, 32, 33.

Such a barrel 101 can advantageously be formed from a single material, for example silicon, without its being necessary to have recourse to transparent optical elements for filtering and guiding the light rays.

The photodetectors 31, 32, 33 may be disposed in corresponding housings so that their respective photodetection surfaces 310, 320, 330 are included in the same plane parallel to the base plane, on a flat side of said cylindrical housings, for example at the bottom of these housings 311, 321, 331.

The source 2 may be disposed in the corresponding housing so that its emission surface lies substantially in this same plane parallel to the base plane, at the bottom of its housing.

Such an arrangement facilitates the integration of the photodetectors and source in the detector.

The cylindrical housings 311, 321, 331 containing the photodetectors 31, 32, 33 preferably have reflective walls for reflecting in all directions the diffused light rays ii reaching the entries of the housings by means of the corresponding light traps, as far as the photodetection surfaces 310, 320, 330.

The cylindrical housing containing a source 2 with small directivity, for example an LED, preferably has reflective walls for reflecting in all directions the light rays emitted by the source 2 as far as the exit of the housing connected to the corresponding light trap, so as to form a beam of incident light rays i. For this purpose, the cylindrical housing is covered with a reflective and/or diffusing paint so as to obtain relatively uniform illumination of the inside of the housing.

Such cylindrical housings advantageously form integrating washers 311, 321, 331 for respectively improving the sensitivity of detection and the quality of illumination of the barrel detector.

These integrating washers 311, 321, 331 can easily be produced by planar manufacturing techniques.

Alternatively, the integrating washers may be replaced by integrating spheres.

Figure 4B:
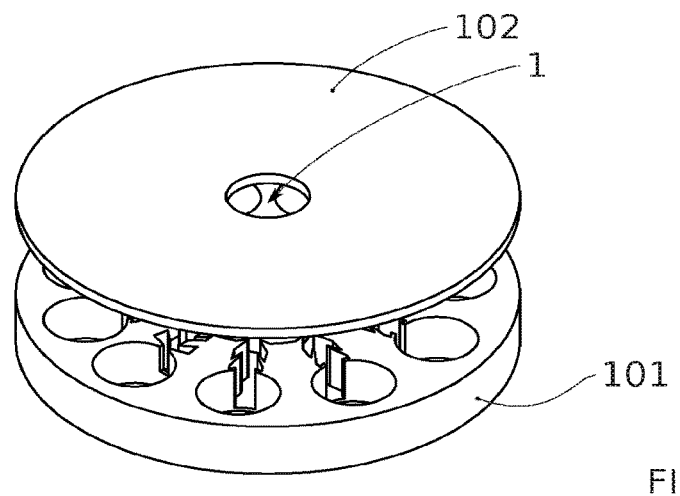
FIG. 4B illustrates the embodiment of the detector in FIG. 4A in perspective with a cover.

The detector also comprises a cover 102 for illuminating external parasitic light (FIG. 4B).

This cover 102 has a hole at the centre thereof so as to form a passage to the channel 1.

The face of the cover 102 facing the cylindrical housings preferably comprises reflective surfaces at these housings.

Figure 4C:
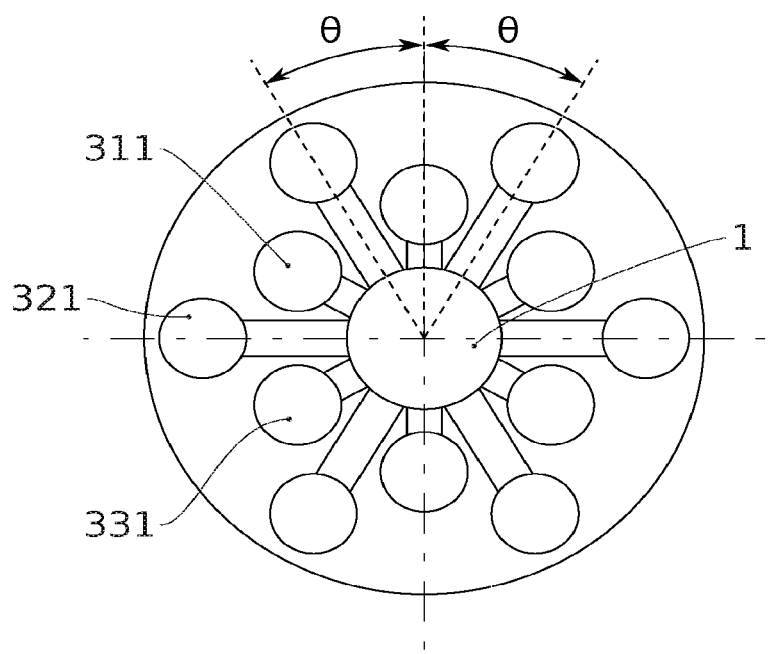
FIG. 4C illustrates, in plan view, an embodiment of a detector according to the invention, wherein the photodetectors are disposed in alternation on two concentric circles.

According to a possibility illustrated in FIG. 4C, the cylindrical housings may be disposed so as to be staggered along two concentric detection circles and along different radii. The cylindrical housings 311, 321, 331 are therefore not necessarily at equal distances from the channel 1. Thus, by making a rotation centred on the axis of the channel 1 in order to sweep the various photodetectors, the latters are disposed in alternation on one circle and on the other.

This arrangement makes it possible to optimise the space requirement related to the cylindrical housings. Consequently the distribution angle θ between two successive photodetectors can be reduced. The angular resolution of the detector can be increased.

These advantages may be further reinforced if the photodetectors are distributed over more than two circles, or in different planes.

For example, the housings situated on the first circle and the housings situated on the second circle may be situated on either side of a mid-plane perpendicular to the longitudinal axis of the channel 1. In this case the optical entries may be centred at the mid-plane, and prisms, guide structures and/or reflective surfaces may reflect or transmit the light rays collected towards the photodetection surfaces of the photodetectors opposite the mid-plane.

The distribution angle θ may be constant along the detection circle or circles, in particular between two successive photodetectors disposed outside the optical axis (○). This makes it possible to perform a symmetrical angular sampling by means of this detector, as illustrated in FIG. 7A.

Alternatively, the distribution angle θ may vary along the detection circle or circles.

Figure 4D:
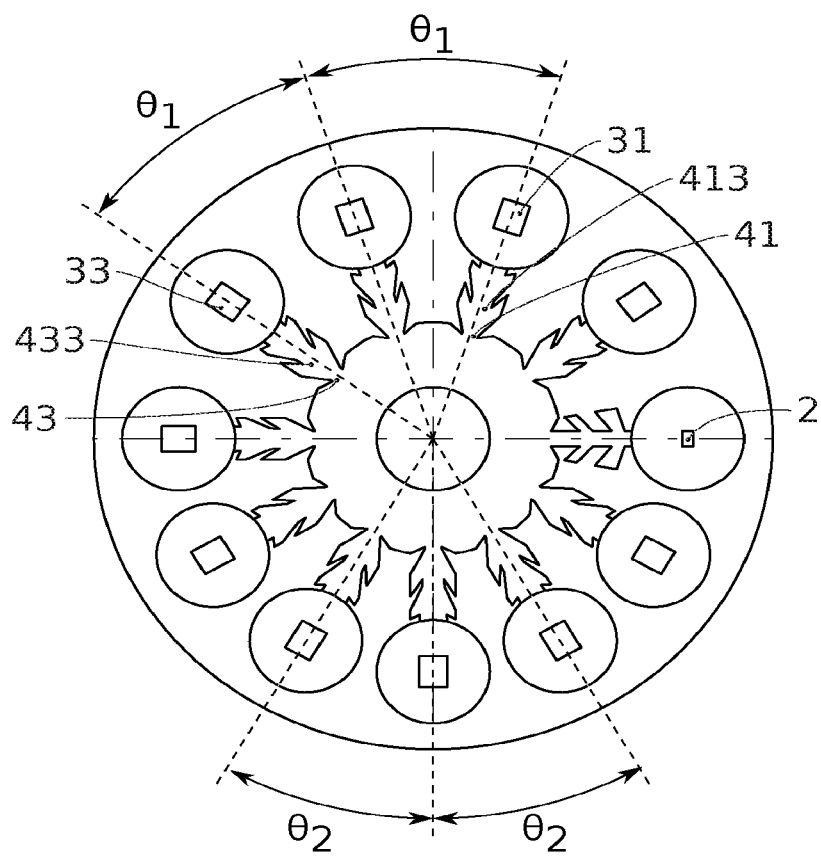
FIG. 4D is another illustration of the embodiment of the detector in FIG. 4A, showing a distribution of the photodetectors in two distribution angles.

According to a possibility illustrated in FIG. 4D, the cylindrical housings containing the photodetectors may be separated by a first distribution angle θ1 on a first half of the detection circle, and by a second distribution angle θ2, different from θ1, on the second half of the detection circle. According to one example, the first distribution angle θ1 may be around 30° and the second distribution angle θ2 may be around 36°. This makes it possible to perform an asymmetric angular sampling by means of this detector, as illustrated in FIG. 7B.

In general, such an asymmetric sampling may be performed by distributing, on a circle around the channel 1, an even number 2n of optical entries of the detector in accordance with: 1 optical entry facing the source, n optical entries on the first half of the circle, spaced apart by an angle $\theta 1 = \pi/(n+1)$ rad, and n−1 optical entries on the second half of the circle, spaced apart by an angle $\theta 2 = \pi/n$ rad.

Figure 8:
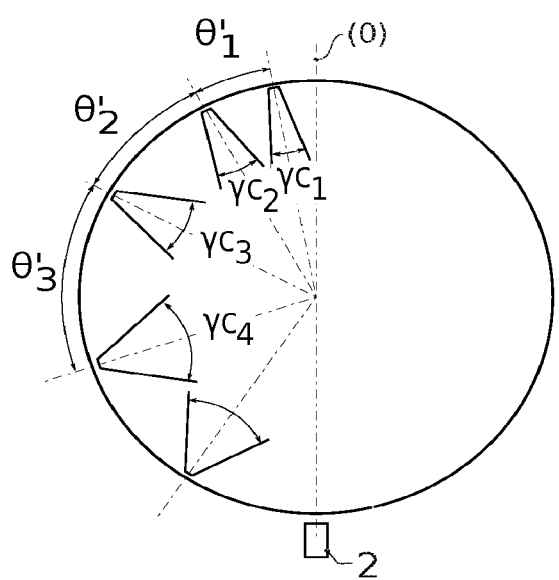
FIG. 8 illustrates schematically another type of angular sampling performed by a detector according to an embodiment of the invention.

According to another possibility illustrated in FIG. 8, the distribution angles θ1', θ2', θ3' ... and/or the aperture angles γc1, γc2, γc3, γc4 ... of the corresponding collection cones vary along the detection circle or circles. It is thus possible to obtain a first type of sampling privileging the angular resolution, for example on a first half or on a first quarter of the detection circle on a side opposite to the source 2, and a second type of sampling privileging sensitivity, that is to say reduction of the measurement noise, for example on a second half or on a second quarter of the detection circle on a side juxtaposed with the circle 2.

FIGS. 6A and 6B illustrate schematically the implementation of a barrel detector according to the invention.

A support 100 made from semiconducting material such as silicon is provided. It may be thinned in advance so as to preserve a thickness of the support 100 of between 500 μm and 1 mm, preferably 750 μm.

A first lithography/etching step forms the cylindrical housings 311, 321, 331, the light traps 414, 424, 434 and part of the channel 1.

The depth of etching for this first step may be between 200 μm and 500 μm.

At the end of the first deep etching step, the housings 311, 321, 331 and the channel 1 are not fully pierced.

A second lithography/etching step next pierces the housings so as to accommodate the photodetectors 31, 32, 33 and the source 2, and the channel 1 so as to allow passage of the fluid comprising the particles.

Alternatively, the piercing may be done by laser micromachining.

The walls and the bases of the integrating washers are next covered with reflective diffusing paint, for example by screen printing or by spraying using a solid stencil.

The cover 102 may be produced separately, from a thinned silicon substrate for example.

It is cut to the dimensions of the barrel 101, pierced at its centre at the channel 1, and covered with reflective diffusing paint on the zones intended to be facing the housings of the barrel 101.

The barrel 101 and the cover 102 are next assembled, for example by adhesive bonding.

According to one possibility, the barrel and the cover are at least partially produced from plastics material and the barrel and cover are assembled by hot swaging. According to one possibility, the assembly is a thermoplastic welding.

According to another possibility, the barrel and the cover are produced by 3D printing. They may be produced in a single piece. In this case, the assembly may not be necessarily.

In the light of the above description, it is clear that the invention proposes an effective solution for improving the angular resolution of the detector while limiting the angular fuzziness and/or the measurement noise.

The invention is not limited to the embodiments described but extends to any embodiment falling within the scope of claim 1.

For example, the detector may comprise a plurality of barrels placed one above the other and/or a plurality of light sources. It may comprise both guide structures of the waveguide type and guide structures of the light trap type.

The invention claimed is:

1. An optical detector for particles, comprising:
   a channel configured to receive a fluid comprising at least one particle and to receive at least one incident light ray;
   a detection system comprising a plurality of photodetectors, each photodetector being configured to receive light rays coming from the channel and diffused by the at least one particle; and
   an angular filtering system comprising a plurality of angular filtering devices each associated with a photodetector of the plurality of photodetectors, each angular filtering device being configured to angularly filter the light rays coming from the channel before reception thereof by the photodetector with which it is associated, and each angular filtering device comprises an optical entry having a numerical aperture smaller than a numerical aperture of the photodetector with which said each angular filtering device is associated.

2. The optical detector according to claim 1, wherein the optical entry of said each angular filtering device is less than or equal to 0.3.

3. The optical detector according to claim 1, wherein said each angular filtering device is configured to define a collection cone at a respective optical entry thereof, each collection cone having an aperture angle $\gamma_c$ of less than 35°, so as to collect diffused light rays having propagation directions having angles of incidence relative to an optical axis of the respective optical entry, of less than 17.5°.

4. The optical detector according to claim 3, further comprising, for at least some of the angular filtering devices, an intermediate optical structure between the channel and the optical entry, the intermediate optical structure being configured so as to reduce divergence of the collection cone and/or to broaden a section of the collection cone of the optical entry, the intermediate optical structure being chosen from among a microlens and a microbead.

5. The optical detector according to claim 1, wherein the channel is cylindrical and the optical entry of said each angular filtering device is distributed at least partly around the channel, along at least a portion of at least one circle.

6. The optical detector according to claim 5, wherein said each photodetector is disposed along at least two concentric circles, in alternation.

7. The optical detector according to claim 5, wherein the optical entry of said each angular filtering device is distributed along a semicircle.

8. The optical detector according to claim 5, wherein the optical entry of said each angular filtering device has an optical axis matching with a radius of a cylinder forming the channel.

9. The optical detector according to claim 1, wherein said each angular filtering device comprises, between an entry thereof and the respective photodetector that is associated therewith, an optical guidance structure from among an optical fibre, a waveguide, a lens, or a light trap.

10. The optical detector according to claim 1, wherein the photodetectors comprise photodetection surfaces disposed in a plane transverse to a longitudinal axis of the channel, the optical detector further comprising an optical integration structure configured to transmit diffused light rays collected at a respective optical entry as far as the photodetection surface of the photodetector associated with the respective optical entry, the optical integration structure being an integrating sphere, an integrating washer, or a prism.

11. The optical detector according to claim 1, wherein the channel is cylindrical and the optical entry of said each angular filtering device is distributed around the channel on axes in line with radii of the cylinder, two successive axes being separated by a distribution angle θ of between 15° and 45°.

12. The optical detector according to claim 11, wherein the distribution angle θ varies around the channel.

13. The optical detector according to claim 11,
wherein a first part of the optical entry of said each angular filtering device is distributed over a first half of a circle and has a first distribution angle θ1 of about 30°, and
wherein a second part of the optical entry of said each angular filtering device is distributed over a second half of the circle and has a second distribution angle θ2 different from θ1, of about 36°, so as to perform a non-redundant sampling of the diffused light rays.

14. The optical detector according to claim 1, further comprising a light source configured to emit the at least one incident light ray through the channel.

15. The optical detector according to claim 14, wherein the light source is isotropic and the optical detector further comprises a device configured to form an incident beam associated with the light source and having an optical exit, and to form, at the optical exit, a beam of incident light rays having an aperture angle of less than 30°.

16. The optical detector according claim 1, having a principal extension dimension of less than 10 mm.

17. A system comprising:
at least one optical detector according to claim 1, wherein the system is chosen from among:
a fire alarm system,
a fire detection system,
a system for analysing quality of a fluid such as air or water,
a pollution alarm system,
an explosive-powder detection system, and
a microbiological-species detection system.

18. A method for manufacturing the optical detector according to claim 1, the method comprising:
providing a substrate;
defining, on one face of the substrate, angular filtering devices surrounding the channel;
forming the channel through the substrate to provide a passage for the fluid;
forming the angular filtering devices on a face of the substrate; and
associating each photodetector with each of the angular filtering devices.

19. The method according to claim 18, wherein the angular filtering devices are light traps formed by etching of the substrate.

20. The method according to claim 18, further comprising forming an optical integration structure configured to transmit light rays from a respective angular filtering device as far as a photodetection surface of the photodetector associated with the respective angular filtering device, the photodetection surface mainly extending on planes parallel to the face of the substrate, and the optical integration structure being an integrating washer etched from the face of the substrate.

21. The method according to claim 18, wherein the photodetectors are disposed on a linear array, and the linear array of photodetectors is associated with a respective angular filtering device.

\* \* \* \* \*